United States Patent [19]

McIntyre

[11] 4,135,089
[45] Jan. 16, 1979

[54] METHOD OF AND APPARATUS FOR PRODUCING IMAGES FOR STEREOSCOPIC VIEWING OF ANNIHILATION RADIATION SOURCES

[76] Inventor: John A. McIntyre, 2316 Bristol St., Bryan, Tex. 77801

[21] Appl. No.: 734,625

[22] Filed: Oct. 21, 1976

Related U.S. Application Data

[63] Continuation-in-part of Ser. No. 548,164, Feb. 7, 1975, abandoned.

[51] Int. Cl.² .................. G03B 35/00; G01T 1/20
[52] U.S. Cl. .................... 250/313; 250/363 S
[58] Field of Search ............. 250/313, 363 S, 309

[56] References Cited

U.S. PATENT DOCUMENTS

| | | | |
|---|---|---|---|
| 3,309,519 | 3/1967 | Euler et al. | 250/313 X |
| 3,329,814 | 7/1967 | Anger | 250/363 S |

Primary Examiner—Saxfield Chatmon, Jr.
Assistant Examiner—T. N. Grigsby
Attorney, Agent, or Firm—Vinson & Elkins

[57] ABSTRACT

A method and apparatus for producing images which may be viewed in three dimensions by use of a stereoscope. In one embodiment, the object to be viewed containing annihilation radiation is placed between a plurality of radiation detectors. The detectors generate signals indicative of the coordinate positions from which the radiation photons originate. These signals are used to display images of the object that can be viewed stereoscopically through a stereoscope. The images may be displayed on two different displays or on a single display in two different colors.

12 Claims, 9 Drawing Figures

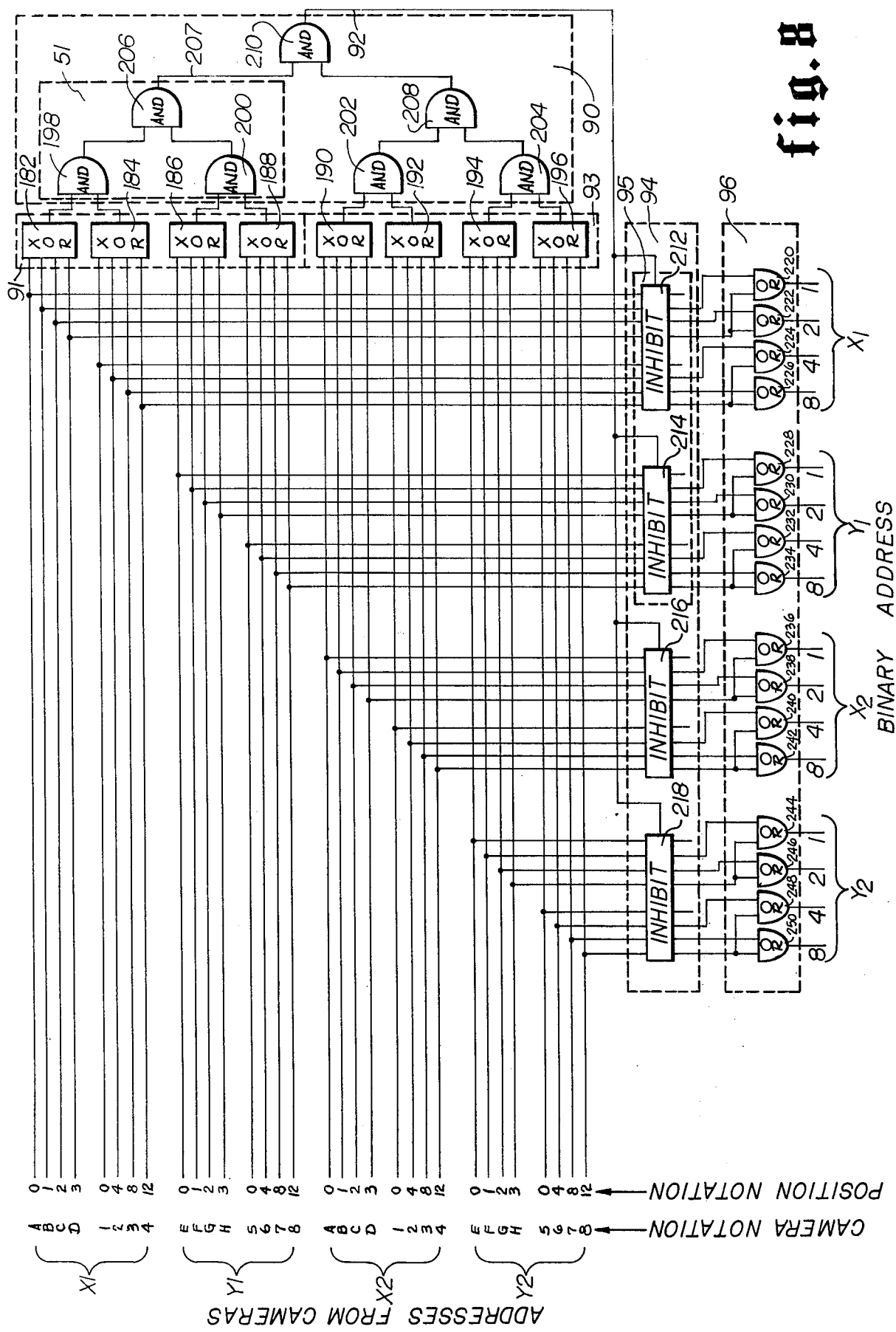

4,135,089

METHOD OF AND APPARATUS FOR PRODUCING IMAGES FOR STEREOSCOPIC VIEWING OF ANNIHILATION RADIATION SOURCES

RELATED APPLICATIONS

This is a continuation-in-part of application Ser. No. 548,164, filed Feb. 7, 1975 and now abandoned.

BACKGROUND OF THE INVENTION

This invention relates to the production of images for stereoscopic viewing of sources which emit annihilation radiation.

In the prior art, no satisfactory method or apparatus has been developed to allow accurate stereoscopic viewing of sources emitting radiation. In the field of medicine, there is a need for the ability of physicians to study selected organs or parts of the human body accurately by perspective viewing without surgery. Heretofore, this problem has not been solved. Also, with the growing use and acceptance of nuclear reactors, there is a need for the ability of scientists to view perspectively nuclear reactor fuel rods to inspect the rods for cracks, defects, etc. in order to prevent equipment malfunctions and to avoid harmful and dangerous accidents. No satisfactory solution to this problem has been determined before the invention described herein.

Also, in studying living systems biologists and physiologists need to observe within these systems the movement of various molecules such as nitrogen, oxygen, and organic molecules. These molecules can be "tagged" with atomic nuclei which emit annihilation radiation. A "camera" which would accurately image in three dimensions the locations of these radioactive molecules would be extremely useful in advancing knowledge about chemical processes in living systems.

In the prior art, it is known that some depth of a three dimensional source object emitting radiation can be perceived by viewing through a stereoscope two pictures of the source taken at different angles. See *Tomographic Imaging in Nuclear Medicine,* Chapter 17, published by the Society of Nuclear Medicine, 1972. This known method uses a parallel-hole collimator to filter out radiation which is not colinear with the holes in the collimator which would otherwise expose the radiation-detecting photographic film. Applicant's invention improves the reconstruction of the radiation source as seen by viewing multiple images stereoscopically by producing images from signals generated only by radiation which would pass through preselected regions in space. This apparatus and method of detection improves the quality of the three dimensional image as viewed through a stereoscope.

For other prior art of general interest, see U.S. Pat. No. 3,652,855 to McIntyre and Saylor (issued Mar. 28, 1972) for "Radiation Image Amplifier and Display Comprising a Fiber Optic Matrix for Detecting and Coding the Radiation Image Pattern" and *Stereoscopy,* pp. 285-289, by N. A. Valyus published by the Focal Press-London and New York.

SUMMARY

Thus, applicant's invention solves the problem of producing images whereby the radiation source is reconstructed accurately through a stereoscope. Annihilation radiation emitted from a radiation source, such as a human thyroid gland containing a radioactive source, is detected by a plurality of radiation detectors in the vicinity of the source. The detectors produce signals which are indicative of radiation which pass through preselected regions in space corresponding to eye positions. These signals are used to produce images which may be viewed through a stereoscope to produce a three-dimensional image of the radiation source.

It is therefore an object of the present invention to produce images from annihilation radiation sources which may be viewed in three dimensions by use of a stereoscope.

It is a further object to provide an improved method and apparatus for producing images from annihilation radiation sources which result in improved stereoscopic reconstruction of said sources.

BRIEF DESCRIPTION OF THE DRAWINGS

The foregoing and other objects, features and advantages of the invention will be apparent from the following more particular description of the preferred embodiments of the invention as illustrated in the accompanying drawings in which:

FIG. 8 is a detailed schematic showing the XOR and INHIBIT circuits of FIGS. 5 and 7.

DESCRIPTION OF THE PREFERRED EMBODIMENTS

Figure 1:
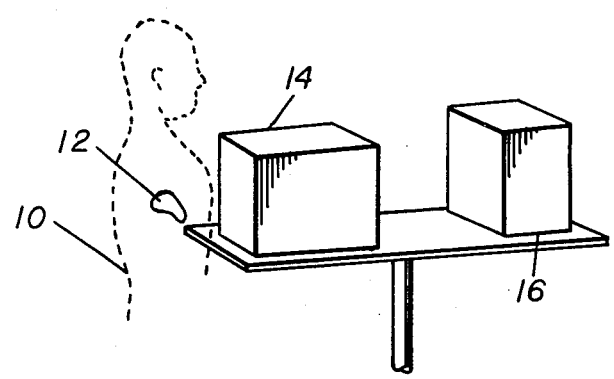
FIG. 1 is a schematic diagram showing the use of a radiation detector in recording images from a human organ implanted with a radioactive substance.

The invention described herein may be used for various applications, including examination of internal organs of the human body. Referring to FIG. 1, a human torso is illustrated having an organ containing radioactive source 12. A converging collimator 14 defining a focal point is mounted adjustably on a stand for directing certain of the radiation from the radiation source onto a radiation detector 16. The detector 16 is positioned in a region between collimator 14 and its focal point, and the plane in which the detector 16 lies is perpendicular to the longitudinal axis of the collimator 14.

The use of collimator 14 and detector 16 is more fully described with reference to FIG. 2. Most radiation sources, such as source 12 emit radiation isotropically. Radiation as that term is used herein may refer to sound, gamma rays, neutrons, mesons, X-rays, charged particles, neutral particles, or any rays in the electromagnetic spectrum. The converging collimator 14 is a device composed of a plurality of hollow tubes whereby the axes of all tubes define a focal point which lies some distance away from the collimator. The tubes of the collimator are made of a material which absorbs radiation which impinges upon it. For many radiation sources such as Technetium 99m ($Tc^{99m}$) and Iodine 131 ($I^{131}$) which may be used as radiation source 12, lead is the preferred material to be used in the collimator 14 to absorb radiation. Therefore, due to the absorption characteristic of collimator 14, the only radiation passing through the collimator is that radiation emitted from the radiation source 12 towards the focal point of the collimator. Collimators are well known in the art and are commercially available from Searle Radiographics Inc. of Des Plaines, Ill. under the trademark DIVCON.

Figure 2:
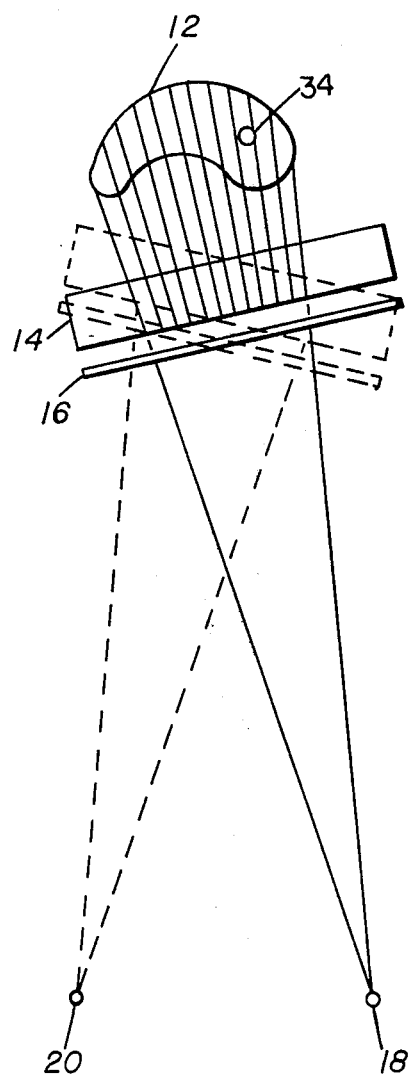
FIG. 2 is a schematic diagram showing how a converging collimator and detector may be used for detection purposes.

As shown in FIG. 2, all radiation passing through collimator 14 impinges on radiation detector 16. Detector 16 may be of planar geometry, although any position sensitive geometry is sufficient, and may be of any material which is sensitive to and detects impinging radiation. If a radiation source 12 such as Technetium 99m is used which emits gamma rays, a sheet of photographic film may be used as the detector 16. If a real time picture of the radiation is desired to eliminate the need for film processing, detector 16 may comprise a bank of phototubes (6) viewing a scintillator (4) and having a discriminator circuit (7) which transforms the phototube signals into X and Y analog signals for input to an oscilloscope (8) as shown in U.S. Pat. No. 3,652,855 (issued Mar. 28, 1972) to McIntyre and Saylor. The specification and all drawings of U.S. Pat No. 3,652,855 are incorporated herein by reference.

The apparatus of FIGS. 1 and 2 is used to produce two stereoscopic photographs. First, collimator 14 is oriented so that its focal point coincides with a first focal point 18. In this position, a photograph of the radiation source 12 is taken by detecting radiation passing through collimator 14. Then, collimator 14 is reoriented so that its focal point coincides with a second focal point 20 spaced apart from the first focal point 18 by a distance corresponding generally to the distance between the eyes of the observer. For most people, the preferred distance has been found to be about 65 millimeters. With collimator 14 oriented to the second focal point 20, a second photograph is taken by recording radiation passing through collimator 14 from radiation source 12.

Figure 3:
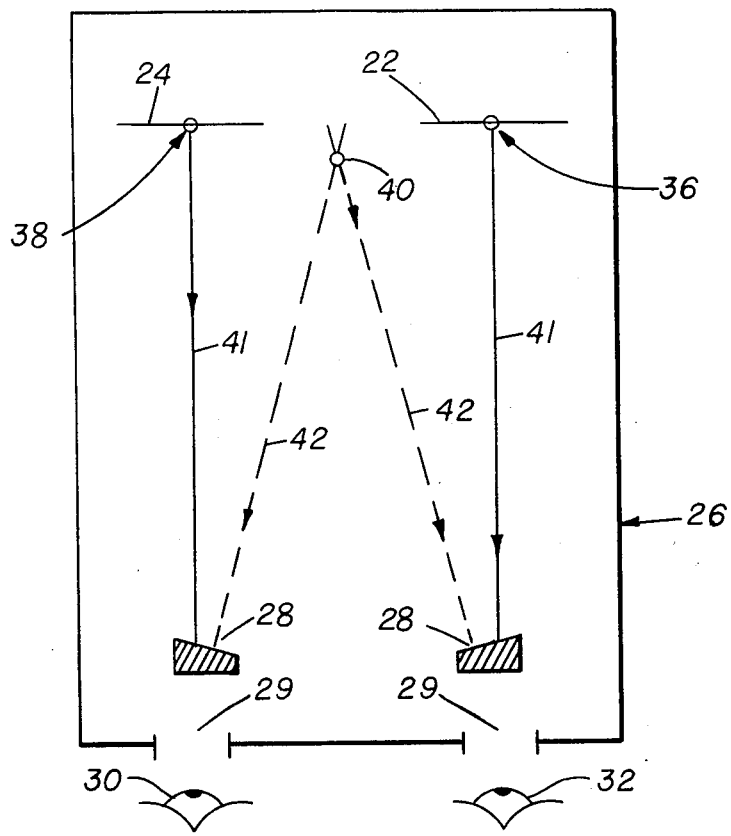
FIG. 3 is a diagram showing the use of a stereoscope to view images produced by the apparatus of FIG. 2.

The first photograph 22 corresponding to collimator 14 oriented with its focal point at focal point 18 and the second photograph 24 corresponding to collimator 14 oriented with its focal point at focal point 20 are then placed inside a stereoscope 26 as shown in FIG. 3. Stereoscopes are known in the art and consist of a pair of refracting wedges 28 which are placed in front of each of two viewing apertures 29 through which an observer looks. A stereoscope which is commercially available which could be used with the invention described herein is manufactured by H. O. V. Optical Co., Inc. of Chicago, Ill. The observer looks through the stereoscope by placing the left eye at a position 30 which corresponds to the position of the second focal point 20 from which photograph 24 is produced and by placing his right eye at position 32 which corresponds to the position of the first focal point 18 from which photograph 22 is produced. The image appears to the observer through stereoscope 26 to lie in a region between the two photographs 22 and 24. Viewing the two photographs 22 and 24 through the stereoscope causes the brain to produce a stereoscopic (or three-dimensional) image of radiation source 12. For example, point 34 in the radiation source appears at point 36 and 38 in photographs 22 and 24, respectively. However, when the photographs are viewed through the stereoscope 26, the image of point 34 appears at position 40 to the observer. Thus, light from positions 36 and 38 on the photographs 22 and 24, respectively actually travel to the eyes of the observer along solid lines 41 in FIG. 3; however, the light appears to the observer to be directed along paths 42 indicated by dotted lines in FIG. 3. This phenomenon results in the observer viewing the image of radiation source 12 stereoscopically since the apparent light path 42 corresponds to the path of radiation from source 12 that passes through collimator 14.

The operation of the apparatus heretofore described is therefore as follows. The object to be viewed stereoscopically is injected with a radiation source 12 by well known methods and means. Collimator 14 is positioned in the region of detection of radiation source 12. A first photographic film is positioned as the detector 16 between the collimator 14 and the focal point defined by collimator 14 and is exposed by the impinging radiation from source 12. The film is removed. The collimator is then reoriented such that the collimator's focal point is displaced by a preselected distance, for example about 65 millimeters. A second photographic film is then positioned as the detector between collimator 14 and its focal point and exposed by the radiation source. The second film is then removed and the first and second films are developed. Both photographs are then placed in a stereoscope whereby a stereoscopic image of the radiation source may be viewed.

ALTERNATIVE EMBODIMENTS

Figure 4:
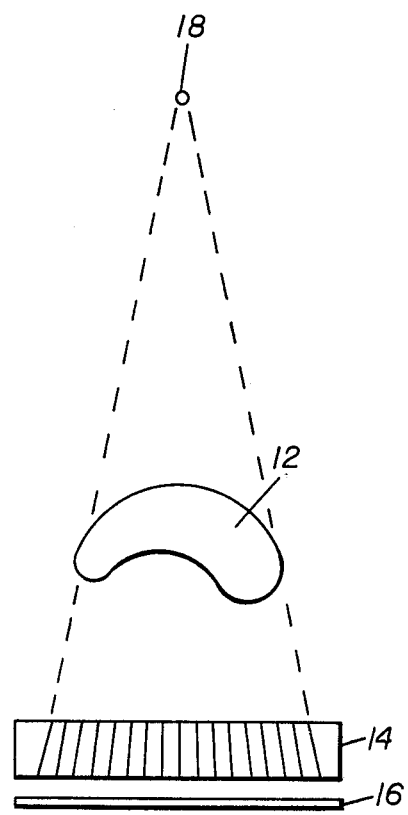
FIG. 4 shows another embodiment of the apparatus of FIG. 2 in which a diverging collimator is used.

An alternative embodiment to the apparatus shown in FIG. 2 is illustrated in FIG. 4 with like reference numerals indicating like components in the two FIGS. However, in the embodiment shown in FIG. 4, the collimator 14 is a diverging collimator rather than a converging collimator. In this embodiment, therefore, the detector 16 records radiation emitted from source 12 which passes through collimator 14 as would be seen by an observer at position 18, the focal point of collimator 14. Thus, the primary difference between the apparatus of FIG. 4 and that of FIG. 2 is simply the perspective (focal point) from which the radiation is detected.

In another embodiment photographic film in the previous embodiments can be eliminated from the viewing process by displaying the images corresponding to the two eyes on two oscilloscope screens. These screens can then be viewed through a stereoscopic system in the same manner as the films were viewed. Or, only one oscilloscope need be used if the images corresponding to the left and right eyes are displayed respectively as red and green (or other suitable colors) images on the oscilloscope screen. The screen is then viewed with a red filter placed in front of the left eye and a green filter placed in front of the right eye. If other colors are used, appropriate corresponding color filters are then used. The use of color filters to create stereoscopic images is known in the art. See, for example, the Aug. 31, 1974 issue of *Business Week*, p. 52A and *Industrial Research*, Nov. 1974, pp. 21–22. See also *Journal of Applied Crystallography*, Vol. 3, Part 5, October 1970, pp. 392–395.

Figure 5:
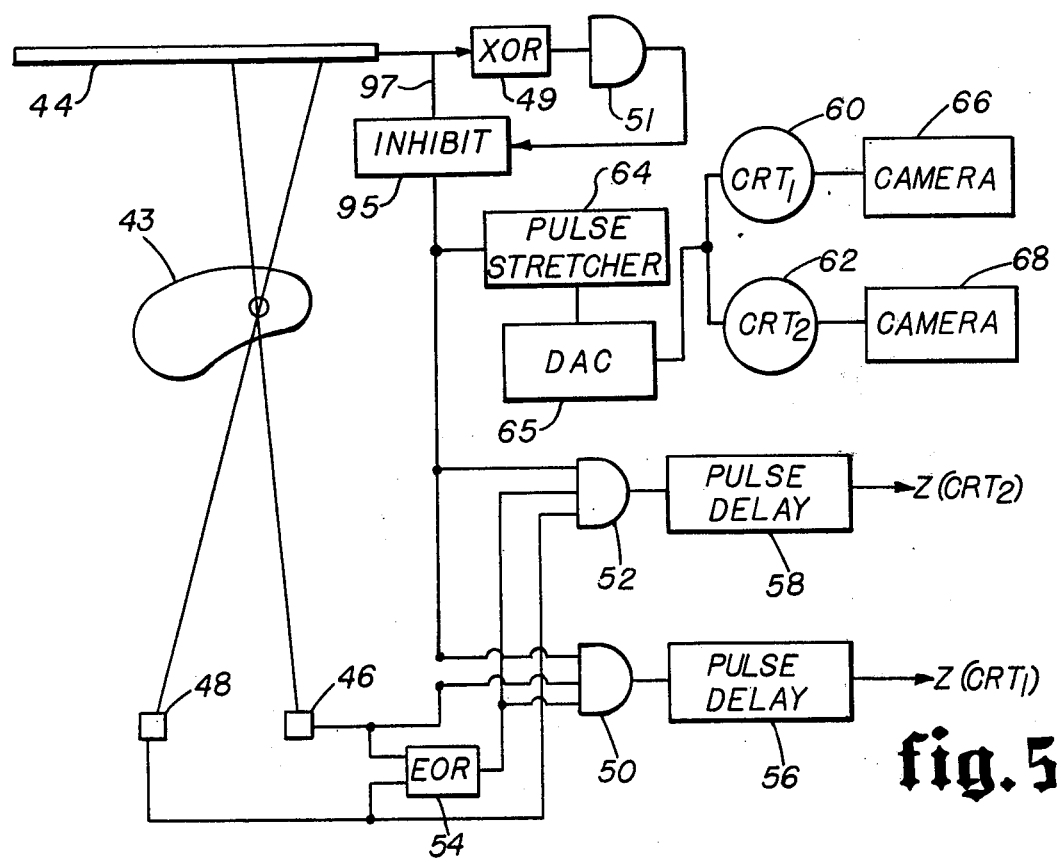
FIG. 5 shows an apparatus and method for producing stereoscopic images from annihilation radiation sources.

Another embodiment of the invention described herein is shown in FIG. 5. In this embodiment the organ or object 43 to be viewed contains annihilation radiation. A characteristic property of annihilation radiation sources is that photons are always emitted in pairs with the photons of each pair traveling in opposite directions.

In this embodiment, the radiation source 43 is placed in a region between a radiation detector 44 which detects radiation impinging on a two dimensional position sensitive detector and two radiation detectors 46 and 48 which detect radiation impinging at regions of small cross sectional area. Detectors 46 and 48 are spaced apart by a preselected distance which may be approximately the distance between an observer's eyes. This preferred distance has been determined to be about 65 millimeters. If the distance between the detectors is not the same as that between the observer's eyes, then the stereoscopic reconstruction of the radioactive object (as in FIG. 3) will produce an image that has dimensions different from the object in both the lateral and the depth directions. Under some conditions such a change in dimensions may actually be desired by the observer. The radiation of interest emitted by source 43 corresponds to photon pairs which impinge on either detectors 44 and 46 simultaneously, or on detectors 44 and 48 simultaneously. Coincidence of impinging radiation on the detectors is determined by gating means. First, the output lines of detector 44 pass through XOR gate 49 and AND gate 51. The output of AND gate 51 is "high" only if only one gamma ray is detected by detector 44 during the pulse interval. A more detailed description of XOR gate 49 and AND gate 51 is given in FIG. 8 and will be discussed later. The output of AND gate 51 controls INHIBIT circuit 95 which allows the X and Y coordinate signals output by detector 44 on line 97 to pass on to other points of the circuit only if AND gate 51 is high. INHIBIT circuit 95 is shown in more detail in FIG. 8. AND gate 50 receives signals from detector 46 and from Exclusive OR gates 49 and 54. When photons are detected simultaneously by detectors 46 and 44, and not by detector 48, the output of AND gate 50 will be a logic "high". The output pulse of AND gate 50 is delayed by delay circuit 56 whose output modulates the writing control (normally, the "Z" input) on cathode ray oscilloscope (CRT) 60. The coordinate signal from detector 44 is stretched by pulse stretcher 64 and is transformed into X and Y deflection signals by digital-to-analog converter (DAC) 65. These deflections appear on the screens of oscilloscope 60 and 62, respectively. The pulse stretcher 64 lengthens the pulse so that the pulse will deflect the oscilloscope beam for an interval longer than the time during which the writing control ("Z") pulse is on. Since the "Z" pulse from AND gate 50 is delayed, the oscilloscope beam is on only after the deflection voltage has been applied and is turned off before the stretched deflection voltage has been removed. Thus, the deflected electron beam is stationary while it is on and produces a dot on the oscilloscope face. The digital-to-analog converter (DAC) 65 converts the digital (X,Y) addresses from stretcher 64 to analog pulses for deflecting the oscilloscope beams.

Similarly, if photons are detected simultaneously by detectors 44 and 48, but not on detector 46, then all inputs to AND gate 52 are logic "high" and an output "high" signal from AND gate 52 results. Pulse delay circuit 58 then delays the pulse which is input to the writing control ("Z" input) of cathode ray oscilloscope 62. In this embodiment, the image of source 43 as it would appear from an eye at detector 46 is thus projected on oscilloscope 60 while the image of source 43 as it would appear from an eye at detector 48 is projected on oscilloscope 62. If oscilloscopes 60 and 62 are "storage" type oscilloscopes, the source images will be recorded on the storage phosphors on the face of the scopes. If non-storage oscilloscopes are used, cameras 66 and 68 can be used with oscilloscopes 60 and 62, respectfully, to expose film in such cameras in order to record the two images of radiation source 43. In this case the shutters of the two cameras would be held open for a time period necessary to collect the image data on the film of the two cameras. All components of the apparatus shown in FIG. 5 are well known in the art. A detector such as detector 44 is fully disclosed in the U.S. Pat. No. 3,652,855 to McIntyre and Saylor which has been incorporated herein by prior reference. Detectors 46 and 48 are known in the art and are commercially available from the Harshaw Chemical Company.

Thus, the operation of this embodiment of the invention is as follows. Two detectors 46 and 48 are spaced apart by a distance preferably equal to the distance between the observer's eyes. The object to be viewed containing annihilation radiation is placed in a region between the two "eye" detectors 46 and 48 and an X-Y detector 44. The shutters on cameras 66 and 68 are opened for a time period sufficient to obtain sufficient image data. Then, the photographs taken by cameras 64 and 68 are placed in the apparatus shown in FIG. 3 for stereoscopic viewing and inspection.

Although the embodiment of the invention illustrated and described in association with FIG. 5 is effective to produce stereoscopic images of annihilation radiation, it is limited to recording only two "eye" positions at one time unless some memory be supplied to store the data from other "eye" positions. Furthermore, the detectors 46 and 48 in FIG. 5 must be small in cross-section (and hence in detection efficiency) if the spatial resolution of the system is not to be degraded. These limitations can be overcome by another embodiment of the invention which also has the advantage that the two detectors required may already be available as part of a general purpose gamma ray camera. This embodiment is shown in FIGS. 6 through 9.

Figure 6:
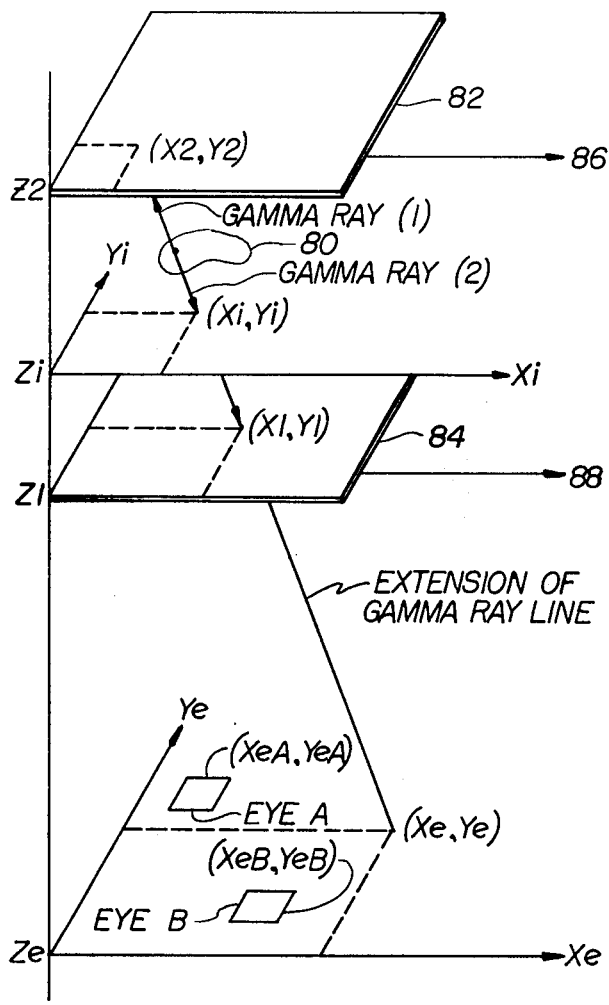
FIG. 6 illustrates diagramatically another apparatus and method for detecting annihilation radiation.

As shown in FIG. 6, an annihilation radiation source 80 (or an object containing annihilation radiation) is positioned between a first radiation camera 84 and a second radiation camera 82. Cameras 82 and 84 may be of the type shown in U.S. Pat. No. 3,652,855 to McIntyre et al. Cameras 82 and 84 each include a means for detecting radiation such as the scintillator screen 4 in McIntyre U.S. Pat. No. 3,652,855 and a means responsive to said detecting means for generating a set of position coordinates responsive to the detecting means such as fiber-optic array 5 and phototube bank 6 in the McIntyre patent.

For convenience, camera 82 is considered to be in a plane Z2 and camera 84 is considered to be in a parallel plane Z1. Coordinate points on camera 82 at Z2 are denoted (X2,Y2) and coordinate points on camera 84 at Z1 are denoted (X1,Y1).

If photons of a photon pair pass through both cameras 82 and 84, then a line in space is defined and the coordinates in a third parallel plane Ze and fourth parallel plane Zi through which the line passes as illustrated in FIG. 6 may be calculated. The Ze plane may be referred to as the "eye" plane since the images created by the apparatus described herein will be generated as if the radioactive source were viewed from various coordinate points on the Ze plane. While the viewing ("eye") locations are assumed to lie in a plane for the purpose of the following analysis, such an assumption is not necessary to fall within the scope of the invention; e.g., the "eye" locations could lie on a spherical surface or be placed at any desired locations in space.

The means and method for calculating the eye coordinates on the Ze plane and the means and method for selectively generating images which would be seen from different eye positions on the Ze plane now will be described.

As illustrated in FIGS. 6, camera 82 generates signals indicative of coordinates (X2,Y2) on cable 86 (containing 16 lines) and camera 84 generates signals indicative of coordinates (X1,Y1) on cable 88 (containing 16 lines) when photons impinge on the detection means of these cameras. Clearly, however, the invention is not limited to having 16 lines on cables 86 and 88 since system configurations having different numbers of lines could be used to implement applicant's concepts.

Figure 7:
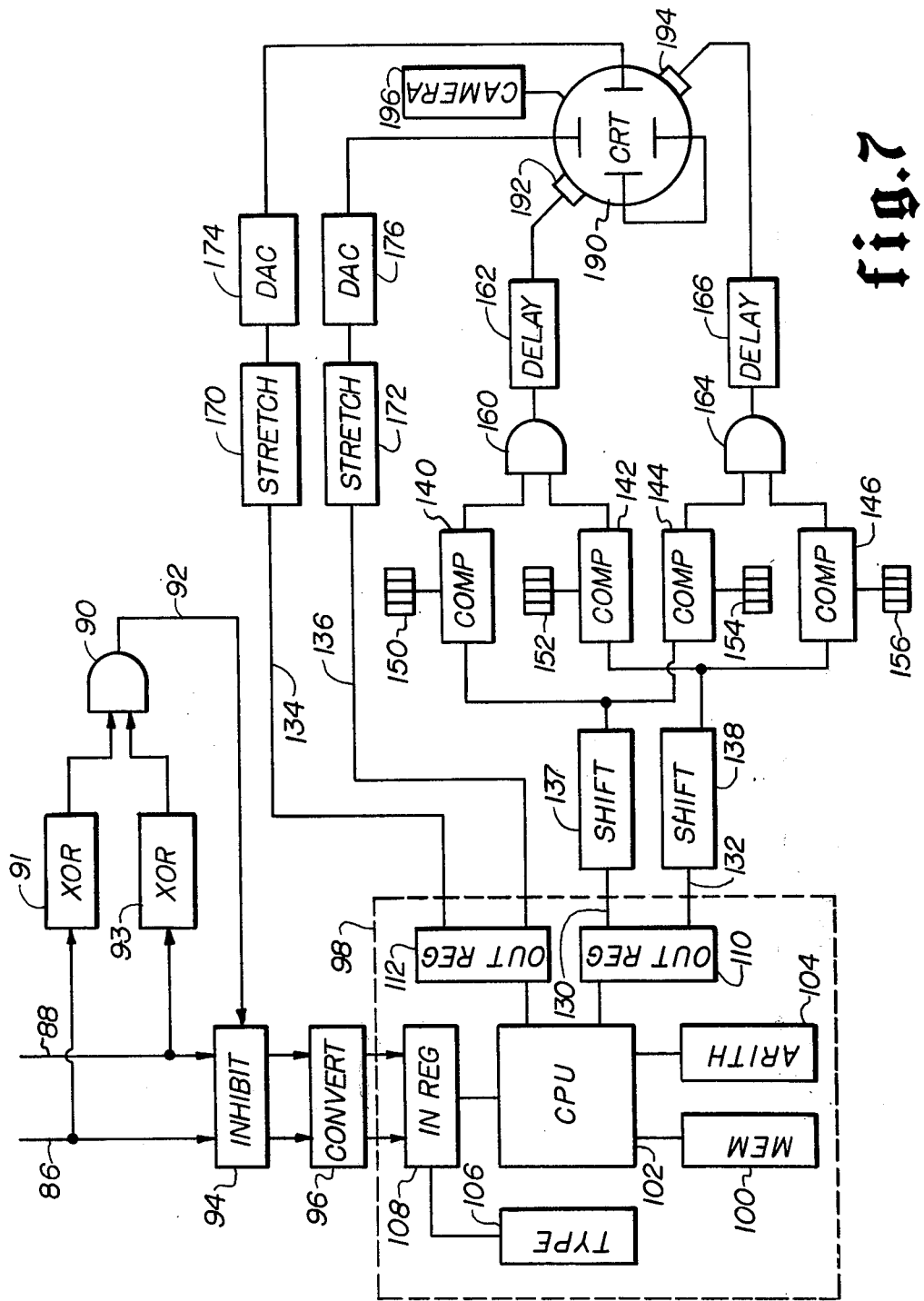
FIG. 7 illustrates schematically the components for manipulating and displaying the image detected by the apparatus of FIG. 6.

As shown in FIG. 7, cables 86 and 88 are input to AND gate 90 by way of exclusive OR (XOR) gates 91 and 93. If photons of a single photon pair simultaneously impinge on camera 82 and 84, then the coordinate signals on cables 86 an 88 and the signals on XOR gates 91 and 93 will cause AND gate 90 to generate a logic "high" output on line 92. The XOR gates 91 and 93 generate a logic "low" signal, thus causing AND gates 90 to generate a logic "low" signal either if no photon is detected, or if more than one photon is detected simultaneously by cameras 84 and 82 respectively. A "high" logic level only allows the signals on cables 86 and 88 to pass through inhibit circuit 94 (described more fully herein below) and then are converted to binary coding by convert circuit 96 (described more fully herein below). The (X2,Y2) and (X1,Y1) coordinates in binary form are then input into a digital computer 98. Computer 98, such as a PDP-11, contains a memory 100, a central processing unit 102, an arithmetic unit 104, a teletype 106, input registers 108 and output registers 110 and 112.

The positions of the Z2, Z1, Zi and Ze planes are known and are input into the computer via teletype 106 through input register 108 as is the positive integer C' (whose value will be selected later).

Computer 98, which is controlled through well-known programming techniques, calculates a constant C based on Z2, Z1, and Ze as follows.

$$C = (Ze - Z1) / (Z1 - Z2)$$

Then, as each new set of coordinates (X1,Y1) and (X2,Y2) is received by the computer, the coordinates (Xe,Ye) of the straight line passing through (X1,Y1) and (X2,Y2), which intersects the "eye" plane Ze, are computed as follows:

$$Xe = X1 - C(X2 - X1) + C'$$

$$Ye = Y1 - C(Y2 - Y1) + C'$$

where the value of C' is a positive integer chosen to be large enough so that Xe and Ye are always positive.

These values of Xe and Ye are output from computer 98 on the two 4-bit lines 130 and 132; they are also stored in the memory 100. Alternatively, the values X1, Y1, X2, and Y2 may be stored in memory 100 so that new values of Xe, Ye may be calculated for different values of Ze.

Also illustrated in FIG. 6 is the "image" plane Zi which is the plane on which the radiation image of source 80 is projected. Zi may be selected in any position near source 80. The coordinate points (Xi,Yi) are also computed by computer 98 in a manner similar to that used for computing Xe and Ye:

$$Xi = X1 + K(X2 - X1)$$

$$Yi = Y1 + K(Y2 - Y1)$$

where $K = (Zi - Z1)/(Z2 - Z1)$.

The calculated values of Xi and Yi are output from computer 98 as 4-bit addresses on lines 134 and 136 respectively; the addresses are also stored in the memory 100 so as to be associated with the Xe and Ye values corresponding to the same radioactive decay event.

In order to determine which values of Xi and Yi are to be used to create the two images for stereoscopic viewing, the Xi and Yi values associated with two "eye" locations A and B are selected for display. The eye coordinates are labelled (XeA,YeA) and (XeB,YeB) as shown in FIG. 6. To select these coordinates, the comparators 140, 142, 144, and 146 are used. A comparator functions so that it produces an output pulse only if the input address agrees with a pre-set reference address already input to the comparator. Such comparators are available commercially as integrated circuits. A simple method for introducing the reference address into a comparator is to connect a thumbwheel switch with digital display to the reference address lines. The thumbwheel switches connected to the four comparators are labelled 150, 152, 154, and 156 in FIG. 7.

The outputs of the XeA and YeA comparators 140 and 142 are connected to AND circuit 160. The output pulse of AND gate 160 is delayed in the delay circuit 162 and then is used to turn on the green electron gun 192 of the cathode ray tube (CRT) 190.

Associated in time with the pulse at the green gun is the (Xi,Yi) address that was computed from the same values of (X1,Y1) and (X2,Y2) as those used to compute the (Xe,Ye) address that activated the green gun. The Xi and Yi addresses are taken from the 4-bit lines 134 and 136, stretched in stretcher circuits 170 and 172 and then converted to analog pulses in the digital-to-analog convertors (DAC) 174 and 176. These analog pulses are connected to the X and Y deflection amplifiers of CRT 190. The deflection of the electron beam of the CRT is, then, proportional to the magnitude of the address of the image at (Xi,Yi). Furthermore, because of the stretching of the X and Y deflection signals, the deflection voltage for the electron beam has attained its proper value before the time-delayed green electron beam is turned on. The beam is stationary then during its period of illumination of the CRT screen since the electron gun is turned off before the stretched deflection voltage signal returns to zero.

The same procedure is used for the gamma ray events which address eye B. In this case, comparators 144 and 146 are set for the coordinates XeB respectively using thumbwheel switches 154 and 156 respectively. Events with Xe and Ye values agreeing with XeB and YeB give output pulses from 144 and 146 and also give an output pulse from AND gate 164 which is delayed by delay circuit 166. This delayed pulse then turns on the red gun 194 of the CRT 190 and a red dot is produced at the (Xi,Yi) coordinate on the CRT screen for a gamma ray event which has emitted a gamma ray directed toward eye B Thus, the CRT 190 displays a green image corresponding to the radiation source as seen by an eye at the preselected position on thumbwheels 150 and 152 (for example, the right eye) while it displays a red image corresponding to the radiation source as seen by an eye positioned at the position preselected on thumbwheels 154 and 156 (for example, the left eye). As the red and green images are displayed on CRT, 190, a standard color camera 196 may be used to record pictures of the images which later can be viewed through red and green filters or, if CRT 190 is a storage oscilloscope, the red and green images may be generated and viewed directly using red and green filters in the manner previously described.

The exclusive OR circuits 91 and 93, inhibit circuit 94, AND circuit 90, and convert circuit 96 shown generally in FIG. 7 are shown in more detail in FIG. 8. The circuit shown in FIG. 8 is designed to use the form of X1, X2 Y1, and Y2 values which are generated by the type of cameras 82 and 84 described in McIntyre et al U.S. Pat. No. 3,652,855. Clearly, if other types of radiation cameras are used, circuits of designs other than that shown in FIG. 8 would be required.

As shown in FIG. 8, values X1 and X2 are each contained on 8 lines and are denoted A, B, C, D, 1, 2, 3, and 4, while values Y1 and Y2 are each contained on 8 lines and are denoted E, F, G, H, 5, 6, 7, and 8. These lines are input, as shown in FIG. 8, to standard exclusive OR (XOR) gates 182, 184, 186 188, 190, 192, 194, and 196. XOR gates 182, 184, 186, and 188 in FIG. 8 correspond to XOR gate 91 in FIG. 7 and XOR gates 190, 192, 194 and 196 in FIG. 8 correspond to XOR gate 93 in FIG. 7. The output values from these XOR gates are input, as shown in FIG. 8, to cascaded AND gates 198, 200, 202, 204, 206, 208, and 210 (collectively denoted gate 90 in FIG. 7) The logic state on output line 92 from AND gate 210 is used to control inhibit circuits 212, 214, 216, and 218. The output values of inhibit circuits 212, 214, 216, and 218 are the input values of such circuits X1, Y1, X2 Y2, respectively, as shown, only when the logic value on line 92 is high; otherwise the output value of such inhibit circuits is zero.

As shown, the output values in inhibit circuit 212 are input to OR gates 220, 222, 224, and 226; the output values of inhibit circuit 214 are input to OR gates 228, 230, 232, and 234; the output values of inhibit circuit 216 are input to OR gates 236, 238, 240, 242; and the output values of inhibit circuit 218 are input to OR gates 244, 246, 248, and 250. These 16 OR gates comprise the convert circuit 96 in FIG. 7. The output of OR gates 220, 222, 224, and 226 yield a binary value for X1; the output of OR gates 228, 230, 232, and 234 yield a binary value of Y1; the output of OR gates 236, 238, 240, and 242 yield a binary value of X2; and the output of OR gates 244, 246, 248, and 250 yield a binary value for Y2.

Figure 9:
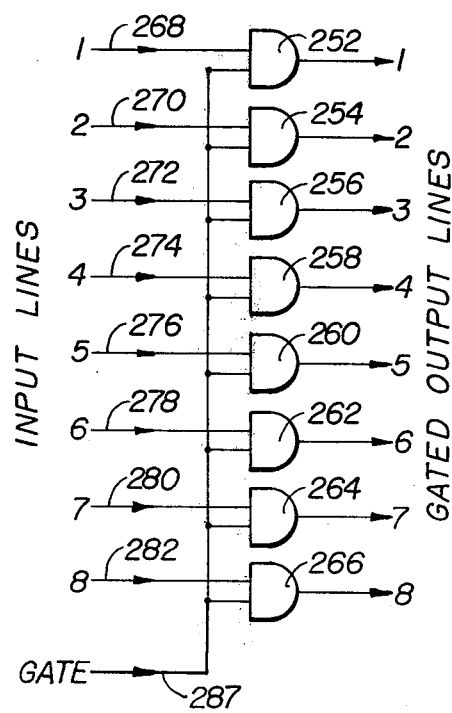
FIG. 9 is a more detailed schematic diagram of the inhibit circuits of FIGS. 7 and 8.

Inhibit circuits 212, 214, 216 and 218 illustrated in FIG. 8 are shown in more detail in FIG. 9. The inhibit circuits comprise eight AND gates 252, 254, 256, 258, 260, 262, 264 and 266 each of which has two input lines, one being a data line (such as lines 268, 270, 272, 274, 276, 278, 280, and 282) and the other being a control line 287. The output values from these AND gates equal the input data values only if the control line is "high"; if control line 287 is low, the output of these AND gates, and thus, the inhibit circuit, is zero.

Finally, there must be a means for selecting the bundle of rays that strike the A and B eye locations in FIG. 6. Since the direction of each ray is already determined by the coordinates (X1,Y1) and (X2,Y2) of detectors 82 and 84, the area of sensitivity for each "eye" can be much larger than the spatial resolution of the detectors. In a sense the "eyes" A and B are similar to a human eye in that the aperture of a human eye is also much larger than the spatial resolution of the eye; the spatial resolution is preserved by focusing the various rays onto the retina which gives a sharp image (corresponding to the well-defined (Xi,Yi) coordinates in the gamma ray instrument) In its acceptance of a large bundle of rays without sacrificing spatial resolution, this instrument is superior to the embodiment shown in FIG. 5. There, the "eye" detectors, 46 and 48, are used to define the direction of the gamma rays so that an increase in the cross section of 46 and 48 to gain more detection efficiency leads to a loss in spatial resolution.

Of course, there is a limitation in the size of the "eyes" that can be used in the instrument. The eye regions must be small enough so that they will be separated just as are the eyes of the observer. Otherwise the steroscopic effects that are obtained by using two eyes till be lost.

Since the area of sensitivity for each eye can be much larger then the spatial resolution of the detectors, a range of addresses for (Xe,Ye) should be accepted for each eye. A simple means for accepting a range of addresses rather than one address, is to shift the data lines downward by a predetermined number of bits. Such a shift in the address lines Xe and Ye is indicated by registers 137 and 138 (which are well known) just before these lines are input to the comparators 140, 142, 144, and 146.

The effect of dropping a number m of the least-significant bits of a binary number is to divide that number by $2^m$ Thus, if two bits are dropped from Xe=25 (binary 11010), the shifted address will be (00110) = 6. Furthermore, if the "eye" address were 27 (binary 11011), its shifted address would also be (00110) = 6 and the address Xe = 25 would be accepted. In other words, if the shifted "eye" address is 6 = (00110), the unshifted Xe address can be (11000) = 24, (11001) = 25, (11010) = 26, and (11011) = 27 and still be accepted. Thus, by shifting the addresses and eliminating m bits, the comparator can be made to accept addresses extending over a range of $2^m$ values.

If address intervals of M which are not equal to $2^m$ are desired, the division of Xe and Ye by M can be performed in the computer to the nearest integer while the comparators will be set for the values XeA/M and YeA/M. Thus, for division of the Xe addresses by 5 in the computer and the comparator set at 4, the undivided Xe addresses of 20, 21, 22, 23, and 24 would be accepted.

The use of four comparators in FIG. 7 has permitted the display on CRT 190 of only those image events (Xi,Yi) associated with the two "eyes" located at (XeA,YeA) and (XeB,YeB). However, all of the (Xi,Yi) addresses and their associated (Xe,Ye) addresses have been stored in the computer memory 100. Thus, two other "eye" locations (XeC,YeC) and (XeD,YeD) may later be selected on comparators 140, 142, 144, and 146, and the memory data (Xi,Yi) and (Xe,Ye) for each gamma ray event sent through the output registers 120 and 122. Those events with the proper new eye addresses will then be displayed as red and green dots on CRT 190. Again, the red and green images so produced can be viewed through red and green filters to produce a steroscopic image as previously described. It is necessary, then, to take only one set of data; these data can subsequently be processed through any pair of "eye"

locations as selected by the comparators to produce steroscopic views of the radiation source from many directions.

Thus, a method and apparatus for producing images from radiation sources which may be viewed in three dimensions by use of a stereoscope have been fully described.

The foregoing disclosure and description of the invention are illustrative and explanatory thereof and various changes in the size, shape and materials as well as in details of the illustrated construction may be made without departing from the scope of the invention.

I claim:

1. An apparatus for producing images for stereoscopic viewing of an object having annihilation radiation therein comprising:
   a first position-sensitive radiation detector;
   a second radiation detector, said second detector designed to sense radiation impinging upon a surface of generally small area, said second detector positioned with respect to said first detector and said object such that photons of a photon pair may impinge simultaneously on said first detector and said second detector;
   a third radiation detector, said third detector designed to sense radiation impinging upon a surface of generally small area, said third detector spaced apart from said second detector by a preselected distance, said third detector positioned with respect to said first detector and said object such that photons of a photon pair may impinge simultaneously on said first and third detectors;
   means responsive to said first and second and third detectors for producing an image of said object which can be viewed stereoscopically;
   said means for producing an image including first means for determining coincidence of impinging radiation on said first and second detectors; second means for determining coincidence of impinging radiation on said first and third detectors; means for generating an image responsive to radiation detected by said first detection means which means for generating is responsive to said first and second coincidence means; and
   means for preventing the generation of said image when said second and third detectors simultaneously sense impinging radiation.

2. The apparatus of claim 1 wherein said first detector means includes a scintillation screen for generating light responsive to impinging radiation and photomultiplier tubes for generating electrical signals responsive to the light generated by said screen.

3. The apparatus of claim 2 wherein said means for generating an image includes;
   discrimination means for converting signals from said photomultiplier tubes to X and Y coordinate signals;
   a first oscilloscope for displaying said X and Y coordinate signals responsive to signals from said first coincidence means;
   a second oscilloscope for displaying said X and Y coordinate signals responsive to signals from said second coincidence means.

4. The apparatus of claim 3 including:
   a first means for recording the image displayed on said second oscilloscope; and
   a second means for recording the image displayed on said second oscilloscope.

5. A method of producing images of an annihilation radiation source for stereoscopic viewing, comprising the steps of:
   positioning a first position-sensitive detector in a region of said source;
   positioning a second detector such that the source is substantially between said first and second detectors, said second detector having the ability to detect radiation passing through a generally small area; and
   positioning a third detector such that the source is substantially between said first and third detector, said third detector having the ability to detect radiation impinging on a generally small area, said third detector located a preselected distance from the area of detection of said second detector.
   generating a first signal upon the occurrence of coincidence of impinging radiation on said first and second detectors;
   generating a second signal upon the occurrence of coincidence of impinging radiation on said first and third detectors;
   generating a third signal corresponding to the position of the impinging radiation on said first detector responsive to either said first or second signals; and
   blocking the generation of said third signal when said first signal and said second signal are generated simultaneously.

6. The method of claim 5 wherein the display means are used to display an image responsive to said third signal.

7. An apparatus for producing images for stereoscopic viewing of an object which generates annihilation radiation, comprising:
   a first position-sensitive radiation detector;
   a second position-sensitive radiation detector, said second detector positioned with respect to said first detector and said object such that photons of a photon pair may impinge on said first detector and said second detector;
   means for generating a first set of position coordinates responsive to photons detected by said first detecting means;
   means for generating a second set of position coordinates responsive to photons detected by said second detecting means;
   means for calculating a third set of position coordinates, said third set of coordinates being indicative of the coordinates where the line defined by a photon pair would intersect a known surface in space;
   first means for comparing said third set of position coordinates with a fourth set of preselected position coordinates, said first comparing means generating signals when said third set of position coordinates are equal to said fourth set of said preselected position coordinates;
   second means for comparing said third set of position coordinates, said second comparing means generating signals when said third set of position coordinates are equal to a fifth set of said preselected position coordinates; and
   means responsive to said signals generated by said first and second comparing means for displaying a plurality of images which may be viewed stereoscopically.

8. The apparatus of claim 7 wherein said means for generating an image includes means for generating said image in color.

9. The apparatus of claim 7 including means for storing said third set of position coordinates.

10. The apparatus of claim 7 including means for storing said first and second set of position coordinates.

11. The apparatus of claim 7 including means for preventing the generation of said image when said first and second detectors simultaneously sense more than one photon.

12. The apparatus of claim 11 wherein said first and second detector means each includes a scintillation screen.

* * * * *